(12) United States Patent
Krahn

(10) Patent No.: US 8,881,609 B2
(45) Date of Patent: Nov. 11, 2014

(54) PERCUSSIVE DRIVING APPARATUS FOR ENVIRONMENTAL SAMPLING OR TEST DEVICE

(75) Inventor: Peter K. Krahn, North Vancouver (CA)

(73) Assignee: Her Majesty the Queen in right of Canada, as represented by the Minister of Environment (CA)

( * ) Notice: Subject to any disclaimer, the term of this patent is extended or adjusted under 35 U.S.C. 154(b) by 721 days.

(21) Appl. No.: 13/020,894

(22) Filed: Feb. 4, 2011

(65) Prior Publication Data

US 2011/0198125 A1 Aug. 18, 2011

(30) Foreign Application Priority Data

Feb. 12, 2010 (CA) ..................................... 2693181

(51) Int. Cl.
| | |
|---|---|
| *G01N 1/04* | (2006.01) |
| *E21B 49/02* | (2006.01) |
| *E21B 11/02* | (2006.01) |
| *G01N 1/12* | (2006.01) |

(52) U.S. Cl.
CPC . *E21B 49/02* (2013.01); *G01N 1/12* (2013.01); *E21B 49/025* (2013.01); *E21B 11/02* (2013.01)
USPC ..................................... 73/864.45; 73/864.74

(58) Field of Classification Search
None
See application file for complete search history.

(56) References Cited

U.S. PATENT DOCUMENTS

| 3,252,514 | A | * | 5/1966 | Joy .............................. 166/376 |
|---|---|---|---|---|
| 4,804,050 | A | * | 2/1989 | Kerfoot .......................... 175/20 |
| 5,313,825 | A | * | 5/1994 | Webster et al. ................... 73/81 |
| 5,474,141 | A | * | 12/1995 | Hart .............................. 175/20 |
| 2011/0179888 | A1 | * | 7/2011 | Danesh ...................... 73/864.44 |
| 2012/0004848 | A1 | * | 1/2012 | Kinast et al. ..................... 702/2 |

OTHER PUBLICATIONS

Technical Report 1902, SSC San Diego, "Coastal Contaminant Migration Monitoring: The Trident Probe and UltraSeep System", Jun. 2003, 56 pages.

* cited by examiner

*Primary Examiner* — Robert R Raevis
(74) *Attorney, Agent, or Firm* — Schmeiser, Olsen & Watts, LLP

(57) ABSTRACT

A percussive driving apparatus for an environmental sampling or test device. The driving apparatus comprises a percussion stem (10), a weighted percussion plunger (20) having a longitudinal bore through which the percussion stem (10) is received, the percussion plunger (20) being slidable along a length of the percussion stem (10), a lift element (80) to permit lifting of the percussion plunger (20) along at least a portion of said length of the percussion stem (10), and a percussion pad (30) affixed to the percussion stem (10) at or near a first end thereof. The percussion pad (30) is configured to receive percussive driving force from the percussion plunger (20). The percussion tube (10) is also adapted at the first end to connect to a probe (40) (for example a shielded or unshielded piezometer, or a split spoon sampler, a seepage meter, long term data logging monitoring device, or seismic device) for environmental sampling and/or testing.

52 Claims, 15 Drawing Sheets

PERCUSSIVE DRIVING APPARATUS FOR ENVIRONMENTAL SAMPLING OR TEST DEVICE

FIELD OF TECHNOLOGY

The present invention relates to environmental sampling methods, and more specifically, to a percussive driving apparatus for an environmental sampling or test device. The percussive driving apparatus can be used for groundwater and soil sampling, or other devices as described herein.

BACKGROUND

Groundwater is found in the spaces between particles of rock and soil, or in crevices and cracks in rock. Much of the earth's fresh water is found in these spaces.

Groundwater flows through the ground and groundwater-bearing formations (known as aquifers), and can enter bodies of surface water such as rivers, creeks, lakes or the ocean by flowing downhill until reaching the groundwater table (the level of soil saturated with water). At this point hydrostatic pressure forces the groundwater up through the bottom sediments, sand, gravel, rock, or cobble into the bottom of the water body.

When groundwater is contaminated by chemicals, they will flow with the groundwater and up-well into the overlying body of water. It is therefore important to be able to collect a sample of this up-welling groundwater just before it up-wells into the body of water, so that its chemical composition and potential toxicity and environmental impact can be determined. However, it can be very difficult and sometimes dangerous to obtain a sample in areas of significant water depth, or where there are multiple factors (such as water depth, fast currents and turbidity) that complicate sampling.

In emergency spill situations, for example train derailments or tanker truck accidents adjacent a body of water, leaking tanks, or leaking effluent lagoons at industrial sites, it is often necessary to quickly obtain up-welling groundwater samples to determine the groundwater quality and zone of impact, to assess cleanup measures and to estimate costs and other impacts. Therefore, a fast, effective sampling device that can penetrate the bottom sediments of the water body and extract the up-welling groundwater before it mixes with the overlying body of water is needed to obtain this information, either for emergency or long term situations.

Devices are available for obtaining welling groundwater samples, such as the Trident Probe co-developed by the U.S. Navy and Cornell University (see for example: Technical Report 1902, "Coastal Contaminant Migration Monitoring: The Trident Probe and UltraSeep System", June 2003, SSC San Diego, San Diego, Calif. 92152-5001). This device is a multi-sensor direct-push sampling device which includes three thin stainless steel probes that can measure seepage rate, temperature and conductivity, and can capture seepage samples. The device can be deployed by hand, from a boat or with the assistance of a diver, and has an "air hammer" system that can be used to help drive the probe tips into the bottom sediments. However, deployment of the Trident Probe is generally limited to calm water and relatively soft bottom conditions, and at deployment depths up to about 30 feet.

Other direct push sampling technologies include large truck or barge-mounted devices, such as the Waterloo Profiler™ and GeoProbe™ devices, which incorporate hydraulic systems to push the probes into the soil or water bed. However, these units are usually quite large and anchoring pylons are needed for barge stabilization in high current flows. These systems are also very expensive to operate, difficult to use in deep waters, and have difficulty penetrating water beds with heavy gravel cobble bottoms.

Therefore, there continues to be a need for a sampling device that can penetrate the bottom sediments of a water body and extract up-welling groundwater in a range of water depth, current and bed conditions. Such a device may also have applications for other sampling and testing methods, such as for obtaining intact core or soil samples, or insertion of long term water quality monitoring and data logging devices, seepage meters or seismic devices.

SUMMARY

The present invention provides an improved apparatus useful for obtaining environmental samples or for environmental testing.

The present invention accordingly relates to a percussive driving apparatus for an environmental sampling or test device. The driving apparatus comprises a percussion stem, a weighted percussion plunger having a longitudinal bore through which the percussion stem is received, the percussion plunger being slidable along a length of the percussion stem, a lift element to permit lifting of the percussion plunger along at least a portion of the length of the percussion stem, and a percussion pad affixed to the percussion stem at or near a first end thereof. The percussion pad is configured to receive percussive driving force from the percussion plunger, while the percussion tube is adapted at the first end to connect to a probe for environmental sampling or testing.

In one non-limiting embodiment, the percussion stem may be a tube adapted at the first end to allow fluid to be conveyed from the probe into the tube. In such an embodiment, the tube may further comprise fluid transport tubing within the percussion stem tube cavity for fluid transfer from the probe into and through the percussion stem tube. The percussive driving apparatus may also further comprise an exit element at or near a second end of the percussion stem tube which defines an exit port through which the fluid transport tubing exits the percussion stem tube. In such an embodiment the percussion plunger will typically be slidable along a length of the percussion stem tube between the exit element and the percussion pad.

As will be appreciated from the detailed description of the invention below, the probe can be a variety of probe types useful in environmental sampling and testing applications. In certain non-limiting embodiments the probe may be a piezometer, a shielded piezometer, a split spoon sampler, a seepage meter, long term data logging monitoring device, or seismic device.

In further non-limiting embodiments of the percussive driving apparatus, the lift element may comprise a lift cord, cable, chain or other suitable lifting means, attached to the percussion plunger.

In addition, the percussion pad may optionally define a recessed hole or groove on the bottom surface thereof with dimensions allowing connection of a probe connector element to the first end of the percussion stem. In certain embodiments it may be advantageous for the recess or groove to encompass the junction between the probe and the first end of the percussion stem.

In a further non-limiting embodiment, the upper surface of the percussion pad (which contacts the percussion plunger) may define a beveled edge at the outer perimeter. Similarly, a lower surface of the percussion plunger (which contacts the percussion pad) may define a beveled edge at the outer perimeter.

If desired, the percussion pad may also comprise a camera anchoring element to secure a camera control line.

The percussive driving apparatus may also further comprise, in a non-limiting embodiment, one or more percussion ballast having a longitudinal bore through which the percussion stem is slidably received. The percussion ballasts may also have beveled edges at the perimeter of at least one surface thereof, preferably the percussion plunger contacting surface.

In another embodiment, which is also to be considered non-limiting, the percussive driving apparatus may further comprise an extension tube which is directly or indirectly connected to the percussion stem at or near the second end thereof. If used in water environments such as lakes or rivers, it may also be advantageous for the extension tube to terminate in an anchor cap, which in turn has a loop, ring or other attachment means to connect to a winch line, rope, cable or other means, for instance to raise and lower the apparatus to and from a boat or barge.

The percussive driving apparatus may also optionally include a mounting plate, attached directly or indirectly to the percussion stem, and which defines at least one aperture through which the lift cord can be passed. In the case of indirect attachment, it is to be understood that the mounting plate can also be attached to the exit element or to the extension tube described above, which are in turn connected directly or indirectly to the percussion stem. In certain non-limiting embodiments, the mounting plate may define a further aperture through which the above-described sample tubing can be passed. In further embodiments, which are also non-limiting, the mounting plate may define yet another aperture and/or an exit slot, to accommodate an underwater camera cable. In this latter embodiment, it may also be desirable to include a quick release clip on the mounting plate to releasably attach said underwater camera cable.

Sampling or test devices or systems, such as but not limited to groundwater or soil samplers which include the above-described percussive driving apparatus, are also provided.

BRIEF DESCRIPTION OF THE DRAWINGS

These and other features of the invention will become more apparent from the following description in which reference is made to the appended drawings wherein.

DETAILED DESCRIPTION

Described herein is a percussive driving apparatus for an environmental sampling or test device. The driving apparatus comprises a percussion stem, a weighted percussion plunger having a longitudinal bore through which the percussion stem is received, the percussion plunger being slidable along a length of the percussion stem, a lift element to permit lifting of the percussion plunger along at least a portion of said length of the percussion stem, and a percussion pad affixed to the percussion stem at or near a first end thereof. The percussion pad is configured to receive percussive driving force from the percussion plunger, and the percussion stem is adapted at the first end to connect to a probe for environmental sampling or testing.

The percussive driving apparatus can form part of a groundwater sampling device which is useful in a range of water bed applications, for example but not limited to gravel, sand and/or mud bottoms. In certain non-limiting embodiments the device can be used to obtain groundwater samples in difficult to penetrate water beds, such as heavy gravel cobble. In other non-limiting embodiments the device can be used in strong current conditions, such as but not limited to fast flowing river beds or in high current ocean situations. Embodiments of the device can also be used in less harsh environments, such as in placid waters in lakes, slow moving streams, rivers or ocean beds.

With reference to the accompanying drawings, an example of an embodiment of the invention is described in the following.

Figure 1:
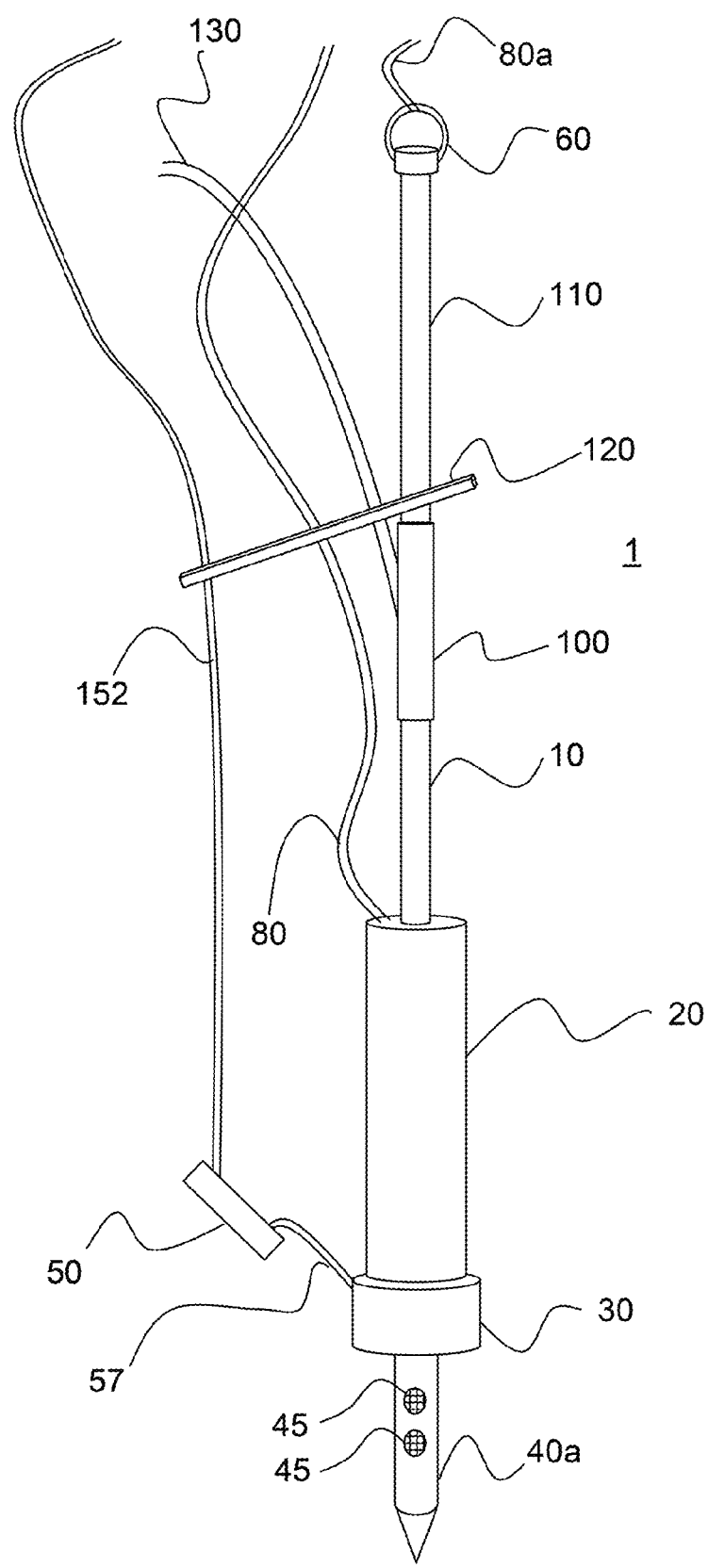
FIG. 1 shows a side perspective view of an example of the percussive driving apparatus used in conjunction with a groundwater sampling device having a piezometer tip, in accordance with an embodiment of the present invention.
Figure 2:
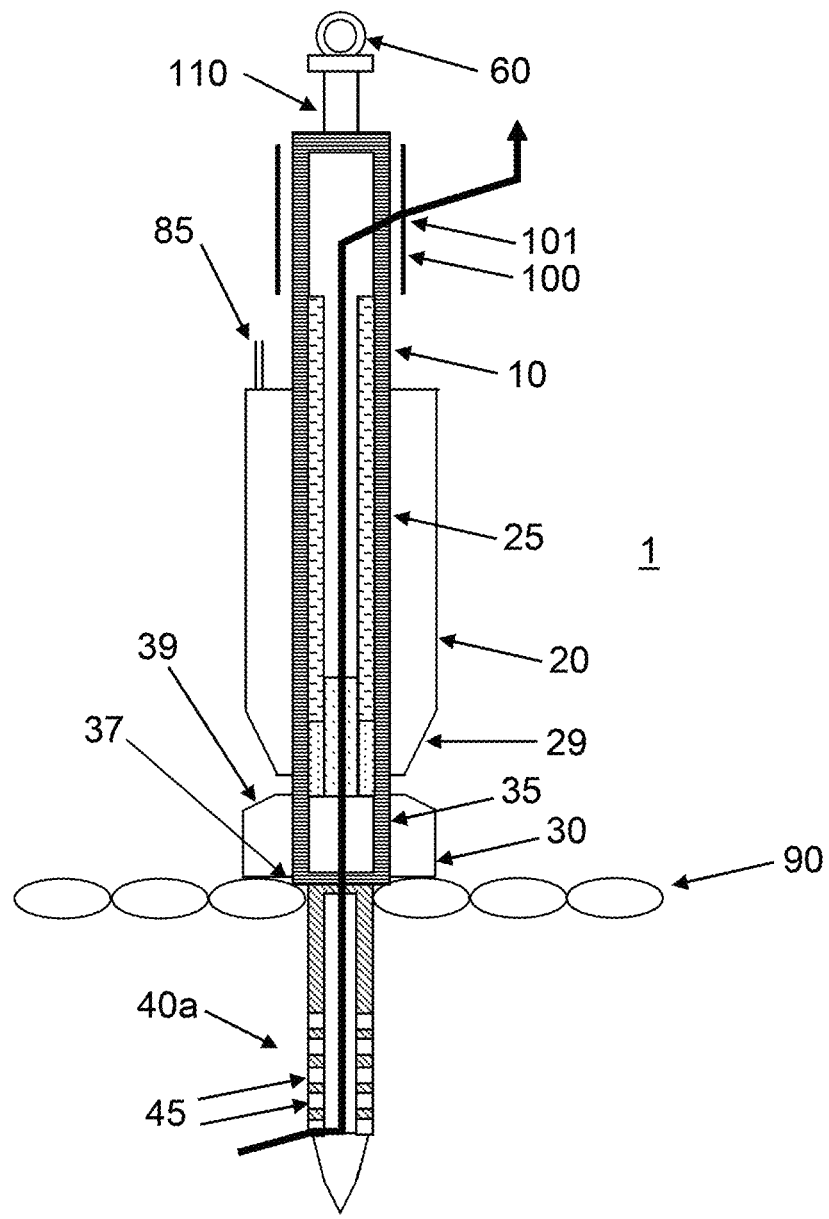
FIG. 2 shows a cross-sectional view of the groundwater sampling device shown in FIG. 1, when inserted into the bottom of a water body.

Referring to FIG. 1, the device (1) includes a percussion stem or tube (10), a percussion plunger (20) and a percussion pad (30). As shown, the percussion plunger (20) is generally concentric, or cylindrical, and has a central bore (25) through which the percussion stem or tube (10) is slidably received (FIG. 2). The percussion plunger (20) is also weighted to facilitate lowering of a probe or sampling tip (40), for instance a piezometer tip, to the bottom of the water body and to drive the probe (40) to a desired depth for groundwater extraction. Similar to the percussion plunger (20), the percussion pad (30) can be cylindrical with a central bore (35) through which the percussion stem or tube (10) is received, and is weighted. The percussion stem or tube (10) is affixed to the percussion pad (30), for instance by welding the percussion stem or tube (10) within the bore (35) of the percussion pad (30), or using other means to provide a secure connection. While shown in the figures as cylindrical, these components can be fabricated using any suitable shape as would be apparent to one skilled in the art.

The probe (40) is fixed to the end of the device (1) in a generally operable configuration. Non-limiting embodiments of the probe (40) include conventional stainless steel drive-point peizometers, shielded stainless steel drive point peizometers, core or soil sampling devices such as split spoon samplers, seepage meters, long term data logging monitoring devices, and seismic devices.

Without wishing to be limiting in any way, the example of a piezometer tip (40a) will be further described with reference to FIGS. 1 to 3. The piezometer tip (40a) may be any desired length, typically ranging from about 0.15 m to 1.0 m and more commonly from about 0.15 m to about 0.30 m in length. In the embodiment shown, the piezometer tip (40a) comprises a stainless steel tube with holes (45) drilled in the side, and which are optionally covered in stainless steel mesh to filter out sand and small particles. Depending on the length of the tip there may be anywhere from one to ten or more holes (45), for example 1, 2, 3, 4, 5 or 6 holes (45). The holes (45) can also optionally be reduced in number or otherwise modified, e.g. by filling with epoxy, to limit water entry to the lower portion of the piezometer and thereby reduce the amount of surface water introduced into the upwelling groundwater sample.

Figure 3:
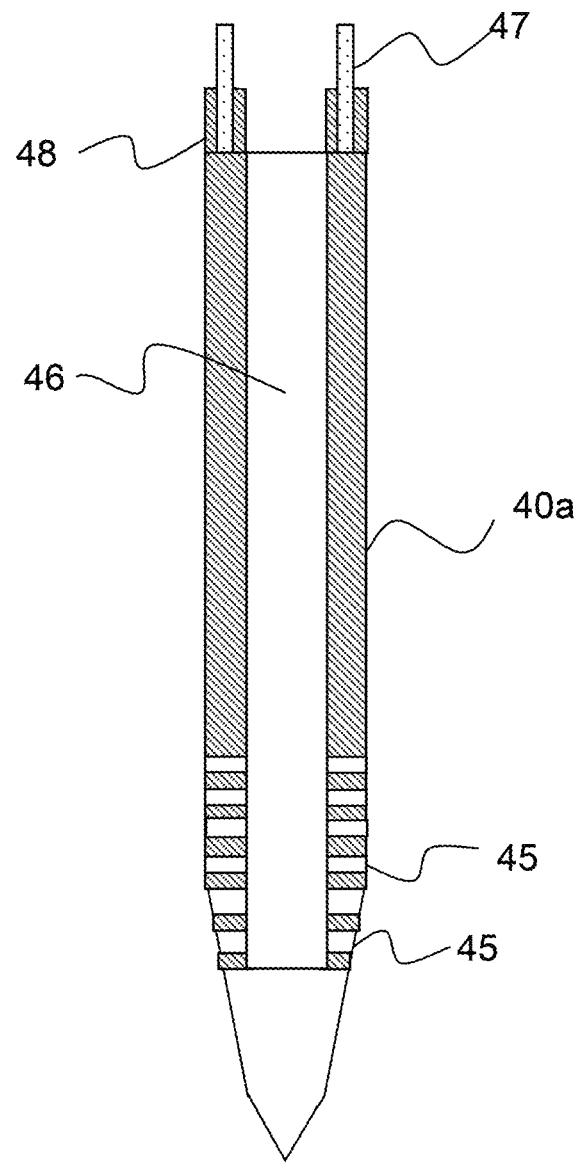
FIG. 3 shows a cross-sectional view of the piezometer tip of the groundwater sampling device shown in FIG. 1.

Referring to FIG. 3, the piezometer tip (40a) will typically have a hollow internal tube (46) terminating in a tubing connector (47) or other attachment means, such as a nipple connector, for the connection of the internal fluid transport tube (46) to a mating connector at the terminal end of the percussion stem or tube (10) and to facilitate conduction of the sample from the piezometer tip (40a) into the percussion stem or fluid transport tube (10). The fluid transport tubing itself may be any tubing commonly used for aqueous sampling, for example polyethylene, Teflon™ or other suitable material.

Figure 4:
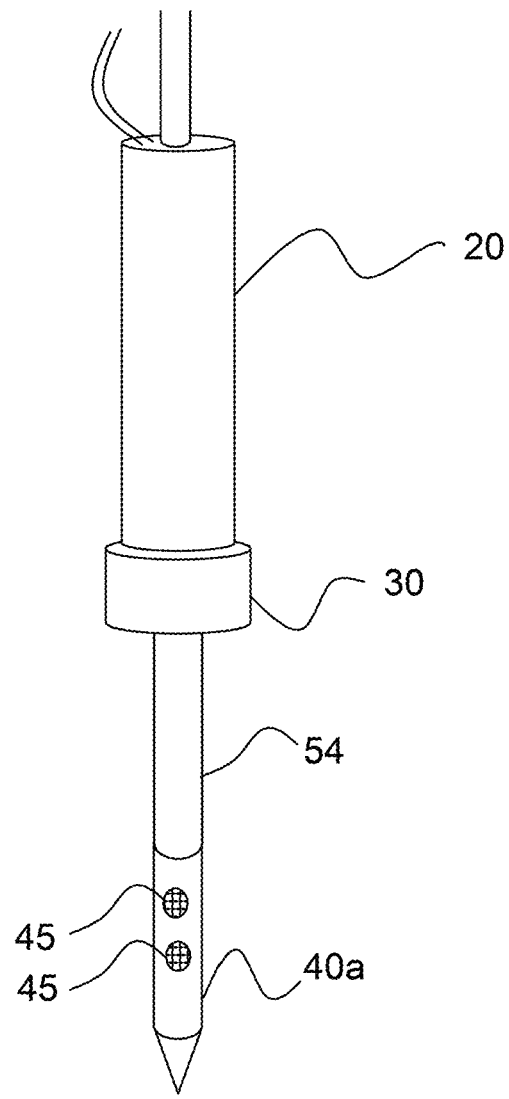
FIG. 4 shows a partial side perspective view of an example of the percussive driving apparatus used in conjunction with a groundwater sampling device incorporating an extension tube, in accordance with another embodiment of the present invention.

The probe (40) may be connected to the percussion stem or tube (10) using any means commonly employed in the art. In the non-limiting embodiment depicted in FIGS. 3 and 4, the piezometer tip (40a) may comprise threads, friction fittings, clamping mechanisms or other means to securely connect the tip to the percussion stem or tube (10) via the terminal connector element (48). In addition, the probe (40) may be connected directly to the percussion stem or tube (10) as shown in FIGS. 1 and 2, or alternately to an extension stem or tube (54) (see FIG. 4) which is in turn coupled to the percussion stem or tube (10). The use of extensions is in certain situations advantageous, for instance in soft bottom applications to allow the user to take deeper samples.

Referring again to FIG. 1, positioning of the device (1) can be aided by an optional underwater camera (50), which allows the operator to view the sample site. This enables highly maneuverable access to sites which are, for example, hazardous due to high current flows or poor visibility, and reduces the need to use a diver or barge mounted system.

The device shown in FIGS. 1 to 4 can be used by hand, or from a boat equipped with a winch system (not shown) to lower and raise the device. In the latter embodiment, an anchor cap (60) or other attachment means is advantageously installed at or near the terminal end of the device (1) to allow it to be attached to the winch cable or, if used without a winch, to an anchoring line. In a non-limiting embodiment, the anchor cap (60) may comprise a stainless steel threaded cap with a stainless steel loop welded to the top for the attachment of the anchor line. The anchor line or winch cable can then be attached to the anchor cap (60) and used to raise and lower the device (1).

The dimensions of the device can be selected according to particular site conditions or otherwise based on the needs of the operator. According to one exemplary yet non-limiting embodiment, the device may be fabricated with a piezometer tip (40a) of from 0.15 m to 0.30 m in length, preferably incorporating the optional silt screen, and comprising a percussion stem or tube (10) with an outside diameter of about 0.025 m. In this embodiment the percussion stem or tube (10) is fabricated using hollow stainless steel pipe with male threads on both ends. While the percussion stem or tube (10) can be any length, for exemplary purposes a length of from 0.60 m to 0.90 m may be selected, for example 0.8 m. The percussion stem or tube (10) is fitted with a circular steel percussion pad (30) which is welded at or near the bottom of the percussion stem or tube (10). In this configuration, the percussion pad (30) is fabricated with a recessed hole or groove (37) on the bottom surface that allows connector element (48) of the piezometer tip (40a), machined with female threads, to connect to the mating male threads at the terminal end of the percussion stem or tube (10). The recessed hole/ groove (37) also protects the piezometer/percussion tube junction.

While the percussion pad may be of any thickness, its dimensions may be selected to create greater or lesser mass. In this particular non-limiting embodiment the percussion pad (30) is about 0.076 m in diameter×0.05 m in thickness, and fabricated of circular stainless steel disk/plate. As an optional feature, which is shown in FIG. 2, the upper surface of the percussion plate can be beveled at the outer perimeter (39). In this exemplary embodiment, the beveled edge extends about 0.015 m at a 30° angle. This beveled angle matches the angle of a corresponding bevel at the outer perimeter (29) on the percussion plunger. While an optional feature, the incorporation of the beveled edges on the percussion pad (30) and plunger (20) is particularly advantageous since it allows water to escape and create greater percussion/energy transfer efficiency.

Figure 5:
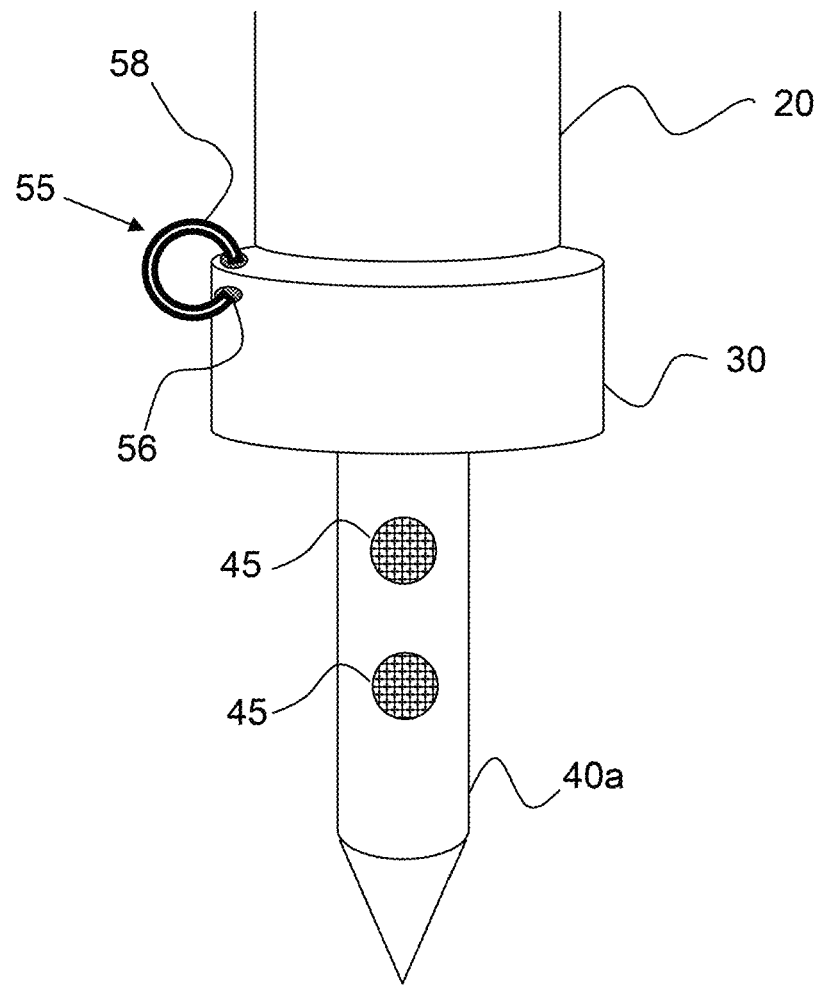
FIG. 5 shows a partial side perspective view of the piezometer tip, percussion pad and camera anchoring element of the groundwater sampling device shown in FIG. 1.

In a further optional embodiment, which is shown in FIGS. 1 and 5, the percussion pad (30) may include a camera anchoring element (55) to secure a camera control line (57). In the exemplary embodiment described above, the anchoring element (55) comprises a hole (56), about 0.003 m in diameter, drilled into the percussion pad (30) to permit direct attachment of the camera control line (57) therethrough. In a further embodiment, the anchoring element (55) may additionally comprise a ring (58) which is passed through the hole (56), and to which the camera control line (57) can be secured. In this particular example, and without wishing to be limiting in any way, the camera control line may be a 2 kg test fishing line. The camera control line (57) is particularly advantageous in fast current conditions to stabilize the camera and reduce camera flutter.

Figure 6:
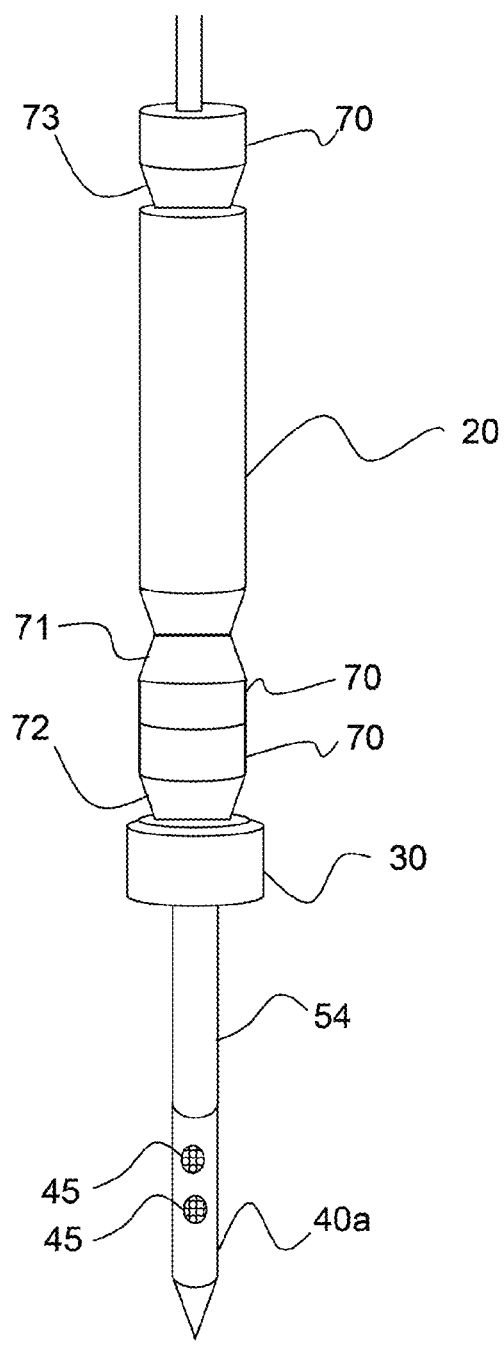
FIG. 6 shows a partial side perspective view of an example of a percussive driving apparatus incorporating percussion ballasts, and beveled edges on the percussion plunger and percussion pad, in accordance with another embodiment of the present invention.

If additional mass is required, for instance when the device is used in fast flowing waters or if the water bottom is difficult to penetrate, percussion ballasts (70) may be added to the device. Referring to FIG. 6, one, two or even more ballasts can be added for greater weight. In a non-limiting example, the percussion ballasts (70) can be modified percussion pads of similar diameter to both the percussion pad (30) and percussion plunger (20), and with similar bore dimensions, for example a 0.076 m diameter×0.30 m long solid stainless steel cylinder with a concentric 0.031 m hole bored through the longitudinal center. The percussion ballasts (70), percussion pad (30) and percussion plunger (20) can also be any other dimension depending on the mass and impact force desired. Without wishing to be limiting, one or more of the percussion ballasts (70) may also be added to the top of the percussion plunger (20) to provide additional mass force. The preferred positioning of the ballast is that the beveled end (73) faces down onto the percussion plunger so as not to interfere with lift chord attachment ring (88) (see FIG. 7).

Referring again to FIG. 6, the bottom surface of the percussion plunger (20) may have an optional beveled edge, for example extending about 0.015 m at a 30° angle. This beveled angle matches the angle of corresponding, yet optional, beveled edges (71,72) on the percussion ballasts (70) and percussion pad (30) and, as mentioned above, allows water to escape and create greater percussion/energy transfer efficiency.

Figure 7:
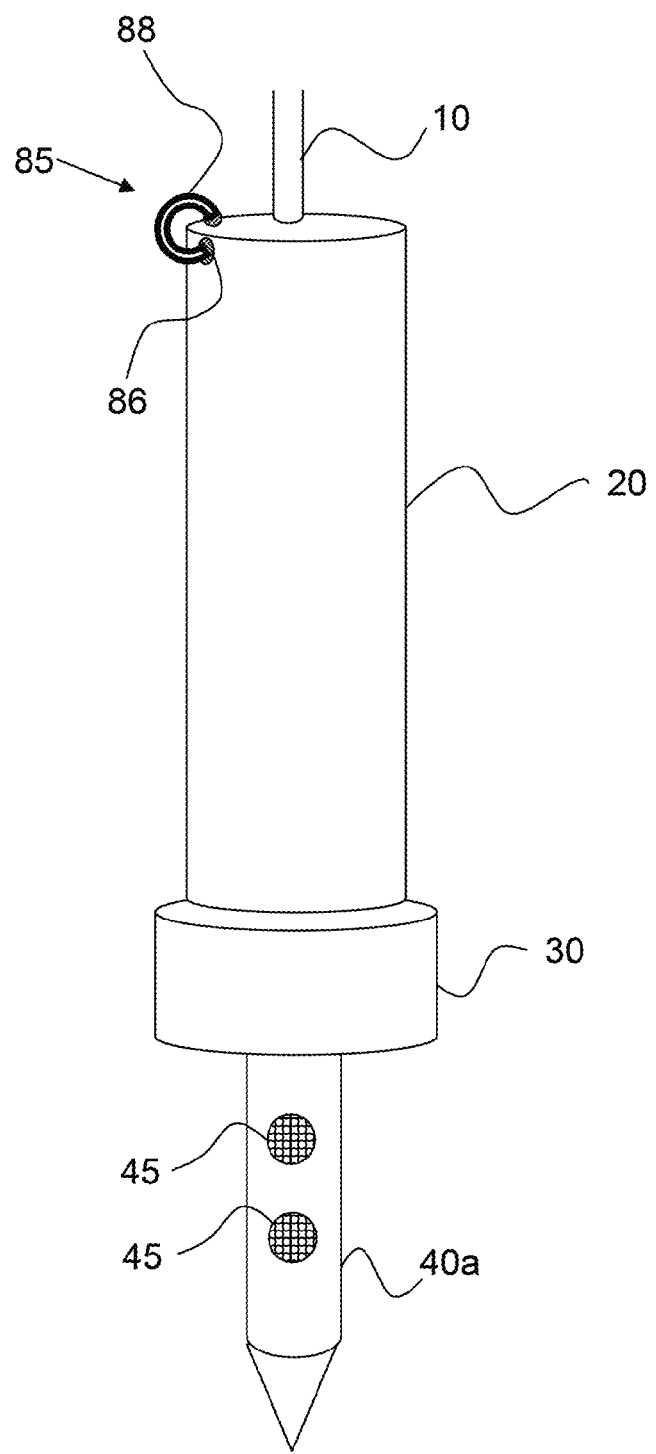
FIG. 7 shows a partial side perspective view of the piezometer tip, percussion plunger, percussion pad and lift cord attachment element of the groundwater sampling device shown in FIG. 1.

The device further includes a lift chord (80) to facilitate the percussive action of the device (FIG. 1). In one non-limiting embodiment, the upper surface of the percussion plunger is modified with a lift cord attachment means (85) (see FIG. 2). The lift cord attachment means may simply be a hole (86) drilled into the percussion plunger (20) to allow for the lift cord (80) to be threaded through and tied off (FIG. 7). As a non-limiting example of such an embodiment, the plunger (20) may have an approximately 0.005 m diameter hole drilled at about a 45° angle at the top of the percussion plunger (20), and exiting the side thereof. In a further possible, yet non-limiting embodiment, the lift cord attachment means (85) may comprise a ring (88) which is passed through the hole (86), or alternatively welded onto the percussion plunger (20), in such a way that the lift cord (80) can be threaded through and tied off.

The lift cord (80) should be of sufficient strength to allow the user to manually raise or lower the percussion plunger (20). In certain embodiments, the lift cord will have a breaking strength of about 50 kg or greater. However, those of normal skill in the art will be able to select the appropriate cord strength and material (for instance polypropylene or similar material). With reference to FIG. 1 and without limiting the choices, the material used for the lift chord (80) which attaches to the percussion plunger and the anchor chord (80a) which attaches to the anchor cap may be of a material such as a natural fiber, a polymer such as polypropylene or metallic strand cable. The material chosen should reflect the operating conditions and hazards of the working environment. With regards to safety and without limiting the material chosen there exists a risk of fouling of the device to the bottom of the water body or to underwater structures. If the device is deployed from a boat in stationary or fast current and the device becomes fouled, there may be a need to cut all chords, cables and tubes in an emergency situation to sacrifice the device in order to prevent a risk of injury to persons, damage to the winch mechanism or flipping of the boat. The choice of material and the tools necessary to effectively cut all chords, cables and tubes should reflect the risk of the stated potential hazards.

As discussed in greater detail above, the percussion plunger (20) is mounted concentrically onto the percussion stem or tube (10) and is dimensioned to allow it to slide up and down at least a portion of the percussion tube length. During operation, the percussion plunger (20) is raised using the lift chord (80) and then the chord is quickly released. The percussion plunger (20) then falls and strikes the percussion ballast(s) (70) or percussion pad (30), thereby creating a driving force which drives the probe (40), e.g. piezometer tip (40a), into the water bottom. Raising and dropping the percussion plunger (20) repeatedly provides impact penetration until the percussion pad (30) comes to rest against the bottom (90) of the water body (FIG. 2).

The device (1) further comprises a sampling tube exit element (100). In the non-limiting example described above, the sampling tube exit element (100) is a stainless steel cylinder, about 0.15 m in length, with female threads on both ends and an angled 0.02 m diameter exit port (101) at the center. The exit element (100) connects to the top of the percussion tube (10) and allows the sample tubing (130) which is connected to the probe (40), e.g. piezometer sampling tip (40a), to exit the percussion tube (10). The top of the sampling tube exit port can be connected to an optional sampler extension tube (110).

The sampler extension tube (110) may be of any desired length and is otherwise dimensioned to allow it to be affixed to the sampling tube exit element (100). In the described non-limiting embodiment, the sampler extension tube (110) is a 0.025 m outside diameter hollow stainless steel pipe with male threads on both ends. A tube length of 0.30 m can be used, which is typical for a deep water system. The optional anchor cap (60) is threaded onto the terminal threads of the extension tube (110).

Figure 8:
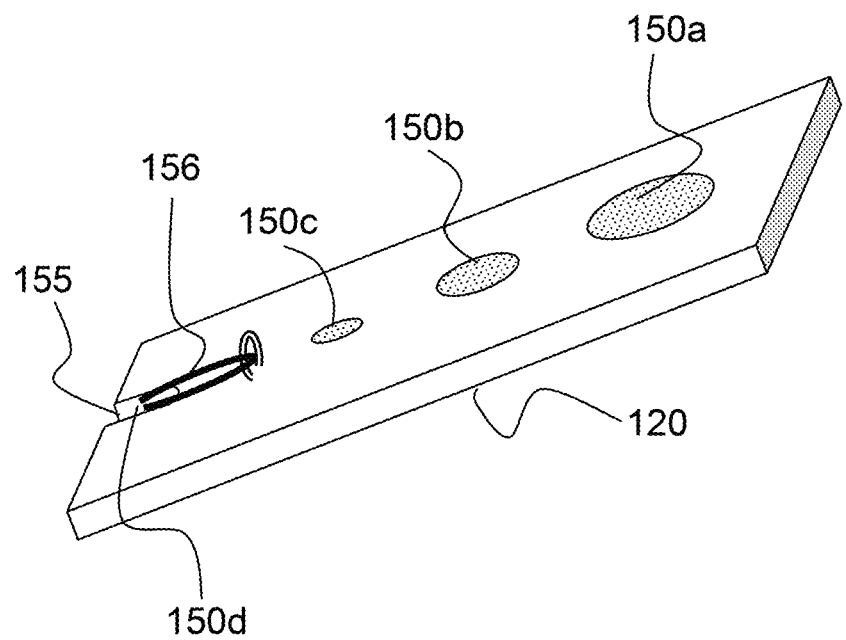
FIG. 8 shows a side perspective view of the mounting plate of the groundwater sampling device shown in FIG. 1.

Installed on the sampler extension tube (110) is an optional mounting plate (120). The mounting plate (120) is particularly useful to reduce tangle of the lift cord (80) and sample tubing (130), and camera cable (152) while in use. In addition, the mounting plate (120) serves as a mount for the optional underwater camera (50). In a non-limiting embodiment, the mounting plate (120) is a Plexiglas plate of about 0.01 m thickness×0.06 m width, and of a length of about 0.13 m or longer. As seen in FIG. 8, holes (150a, 150b, 150c) are drilled along the midline to accommodate the dimensions of the sampler extension tube (110), sample tubing (130), the lift cord (80), and/or any other cables or tubing that may be used in the device. In the exemplary embodiment described above, three holes are drilled in the mounting plate (120) of about 0.026 m, about 0.02 m and about 0.007 m in diameter to receive/secure the sampler extension tube (110), sample tubing (130), and lift cord (80), respectively. A fourth optional hole (150d) is also drilled into the mounting plate (120) of variable diameter, with an exit slot (155), to accommodate an underwater camera cable (152).

The mounting plate (120) keeps the percussion tube (10), sample tube (130), percussion plunger lift cord (80), and camera cable (152) in a straight line with respect to the device during operation, and prevents them from tangling. This configuration also creates a "drag fin" which reduces the tendency of the unit to spin in fast currents. If the fourth optional hole (150d) is also provided for the underwater camera cable (152), the mounting plate (120) can advantageously be manufactured with increased length and include a quick release clip (156) to releasably attach the underwater camera cable (152). Clip (156) facilitates adjustment of the underwater camera (50) to a depth appropriate for viewing of the probe (40), determining of a suitable location for insertion, and verification of successful insertion into the water bottom. The clip (156) is also particularly useful in the event that the device becomes fouled, in which case the underwater camera cable (152) can be given a sharp pull to free the underwater camera cable (152) from the clip (156). The camera cable (152) can then slide out of the exit slot (155) and be pulled from the water, facilitating recovery of the camera (50) separate from the device (1). Other measures can then be taken to recover the fouled device (1) without concern for damaging the camera (50).

Figure 9:
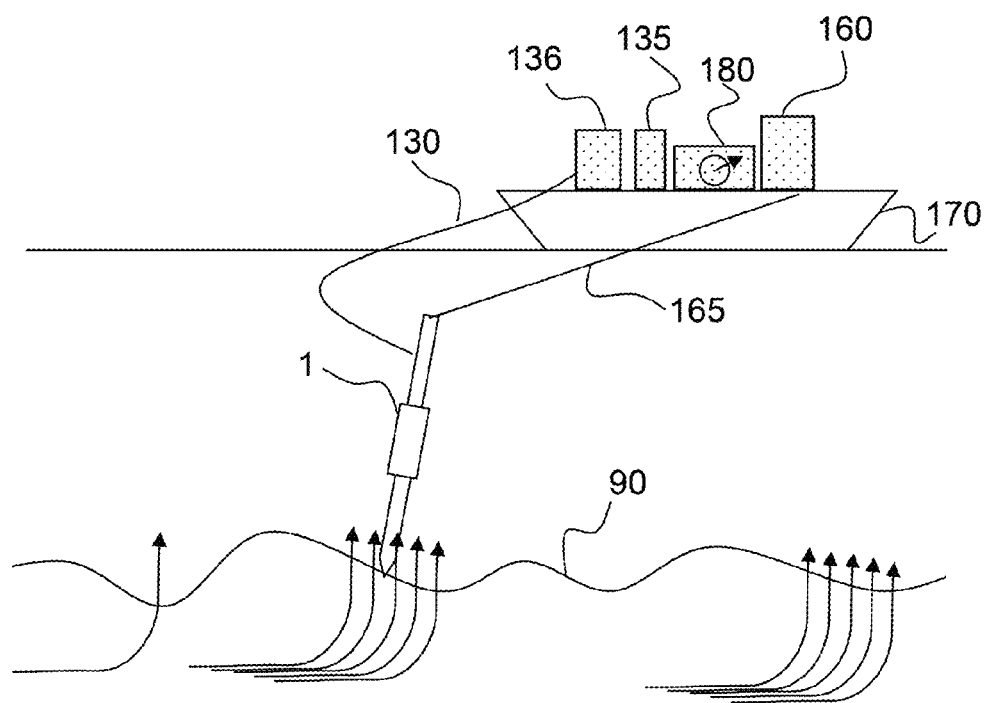
FIG. 9 shows a schematic view of the operation of the groundwater sampling device shown in FIG. 1, prior to insertion into the bottom of a water body.
Figure 10:
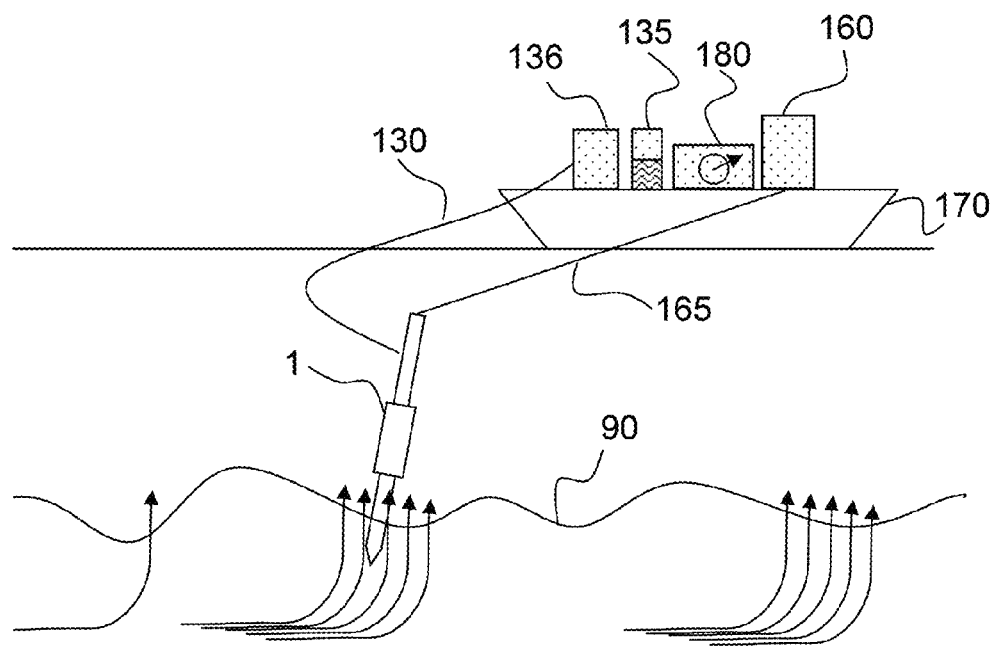
FIG. 10 shows a schematic view of the operation of the groundwater sampling device shown in FIG. 1, following insertion into the bottom of a water body.

General Operation of the Device:

Using the non-limiting example of a large cobble, fast flowing river at greater than 3 meters depth, and referring to the simplified schematics shown in FIGS. 9 and 10, a winch system (160) may be used to lower the device (1) until the probe (40) (e.g. a piezometer tip) just touches the river bottom (90) (FIG. 9). The underwater video camera (50) (not shown), provides a view of the placement of the device (1). The percussion plunger lift cord (80) (not shown) is then raised to lift the percussion plunger (20) to the upper limit of the percussion tube (10) and then the cord (80) is released allowing the percussion plunger (20) to fall and strike the percussion pad (30). The mass of the plunger (20) impacts on the percussion pad (30) and drives the piezometer tip (40) into the river bottom (90). The percussion plunger (20) is raised and dropped repeatedly until the percussion pad (30) contacts the river bottom (90) (FIG. 10).

Groundwater Sample Extraction:

If low flow rate is required, a sample of groundwater can be extracted using only the existing water pressure due to the height of the water column above the river bottom (90), which will force groundwater into the piezometer screens (45) and up the sample tube (130) (see directional arrows showing the water path through the device (1) in FIG. 2). However, the groundwater will only rise to be equal to the surface of the river. In addition, flow is usually too slow, therefore a variable flow rate peristaltic pump (136) may be desirable to facilitate sample extraction. The variable flow rate peristaltic pump (136) can be attached to the upper end of the sampling tube (130), and configured to outlet to a sample reservoir, such as sample bottle (135). If a low flow rate is desired, this can be achieved by using the variable flow rate pump after the sample tube (130) is filled to the water surface, and using the variable flow rate pump to raise the water in the sample tube (130) into the sample bottle (135) in the boat (170). The variable flow rate peristaltic pump (136) can also be used at a variable rate to accelerate the groundwater extraction, keeping in mind the need to minimize drawing in any water from the overlying stream, river, lake or ocean which could dilute the samples. In certain non-limiting embodiments, flow rates as low as about 0.1 to 5 liters/minute should be achievable depending on the porosity of the river bottom. In addition, additional sampling components and devices may be used according to normal procedures, for instance to incorporate a conductivity meter (180) to aid in determining when to collect samples from the tubing. Groundwater samples can be collected and preserved according to normal sampling protocol as would be apparent to those skilled in the art.

Extraction of the Device:

The device (1) has penetrated the river bottom (90) and needs to be extracted once the sampling is complete. The winch system (160) may be sufficient to extract the device (1). If assistance is required, a reverse process of pulling the percussion plunger lift cord (80) sharply upward so that the percussion plunger (20) strikes the sampling tube exit element (100) to produce an upward force. This upward force assists in extracting the probe (40) from the gravel bottom. These upward pulls are repeated until the device (1) is freed from the substrate and retrieved using the winch system.

Further additional embodiments of the invention will now be described with reference to FIGS. 11 to 14.

Split Spoon Sampler:

The percussive driving apparatus described herein can also be used with a split spoon sampler as will be described in further detail below.

Split-spoon samplers comprise a metallic tube that can be driven into and extracted from soils and sediments to collect a soil sediment "core sample", which provides a column profile that can be sub-sampled and tested to determine physical and chemical characteristics such as pollutants. They are typically used together with a hydraulic mechanism which forces the sampler into the soil sediment on land or in shallow water. The metallic tube typically comprises a sample entry port (190) to permit the core sample to enter the sampler, an internal ball valve (195) to allow escape of fluids during insertion and retention of sample during extraction, as well as a fluid exit port (197).

According to this embodiment of the invention, the probe (40) of the percussive driving apparatus is a split-spoon sampler (40b, 40c, 40d) which is connected to the percussion stem or tube (10) in place of the piezometer described above and shown in FIGS. 1 to 10. Core sampling is therefore undertaken by driving the probe (40), or in this case the split-spoon sampler (40b, 40c, 40d), into the terrain using percussive force and avoids the need for more cumbersome and expensive hydraulic mechanisms.

Figure 11:
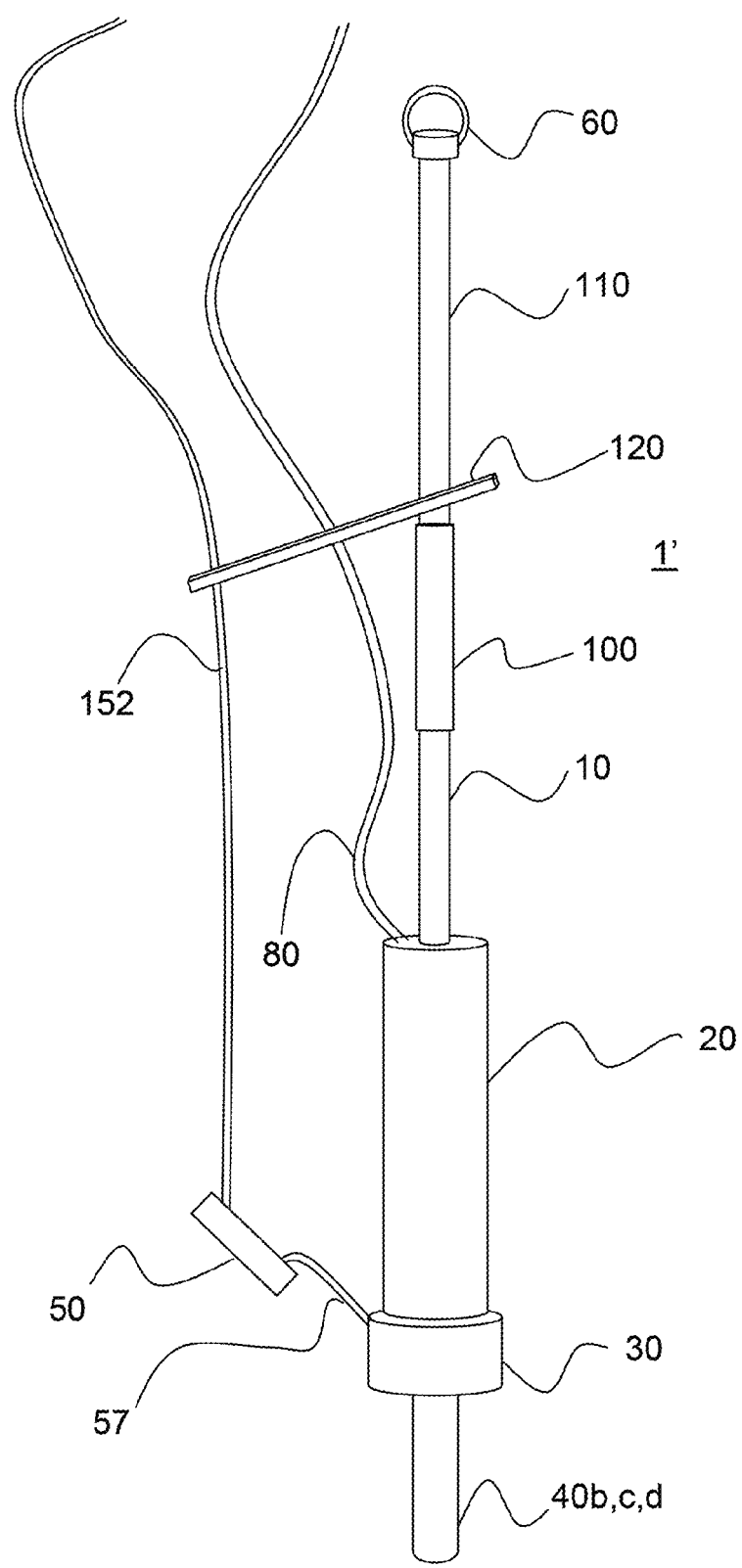
FIG. 11 shows a side perspective view of an example of the percussive driving apparatus used in conjunction with a soil sampling device having a split spoon sampler, in accordance with another embodiment of the present invention.
Figure 12:
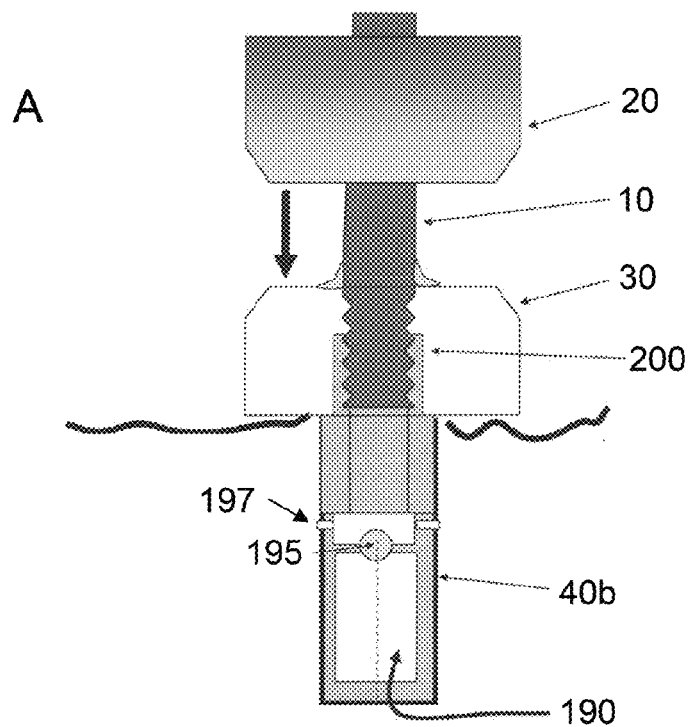
FIG. 12 shows a cross-sectional view of three examples (A, B and C) of embodiments of the split spoon soil sampling device shown in FIG. 11; following insertion into soil or the bottom of a water body.
Figure 12:
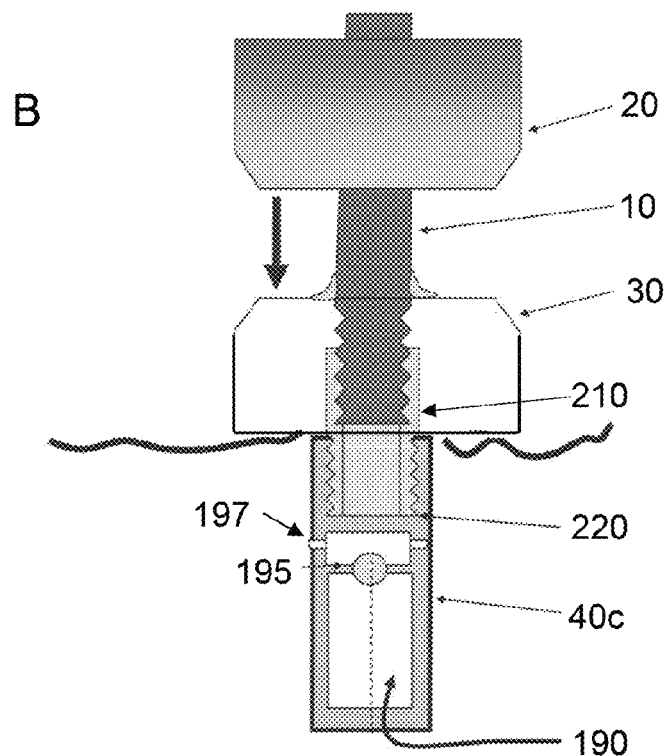
Figure 12:
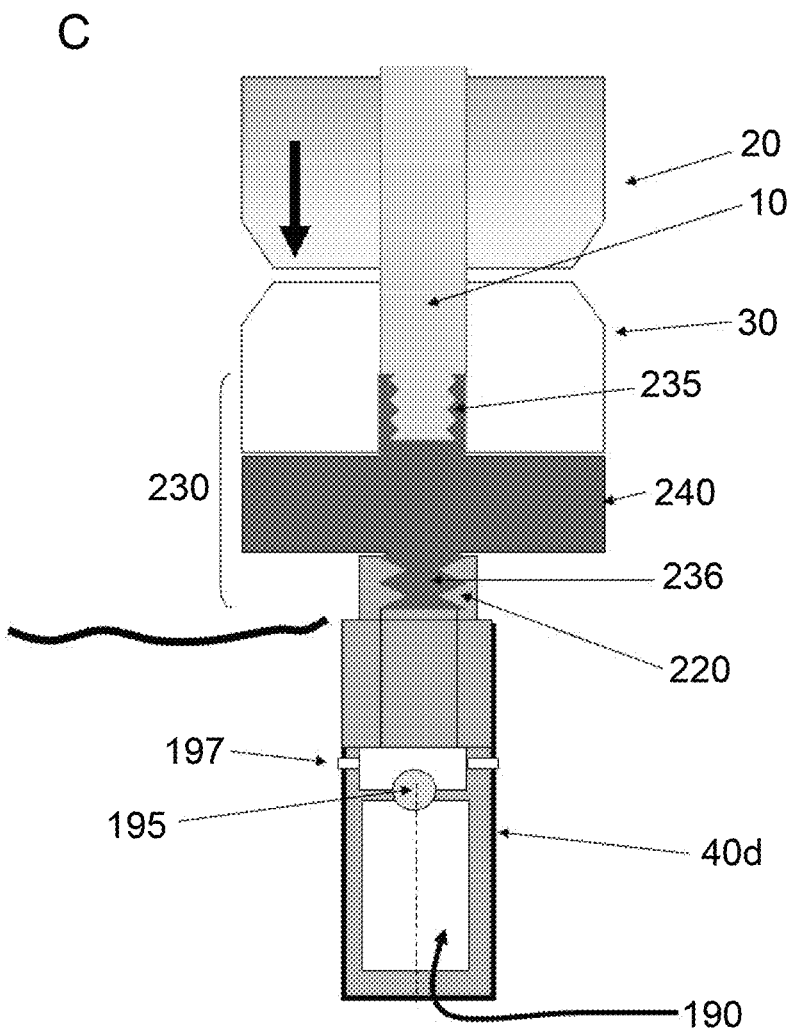
Figure 13:
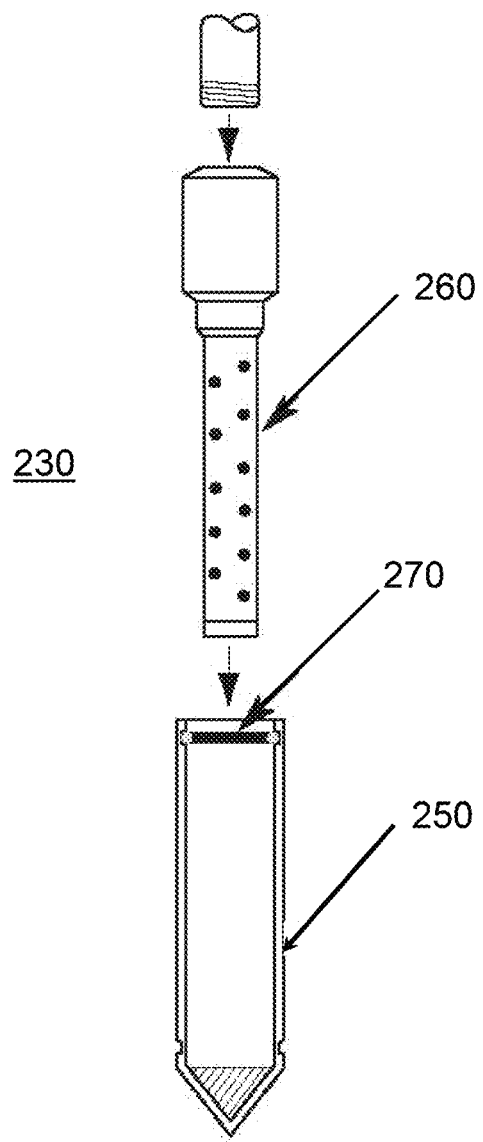
FIG. 13 shows a partial cross-sectional view of a prior art shielded piezometer tip, separately showing the shield and piezometer components.

With the exception of the probe (40), the elements of the percussive driving apparatus are similar to those described above. Referring to FIG. 11, the device (1') includes similar elements to those shown in FIG. 1, including a percussion stem or tube (10), a percussion plunger (20) and a percussion pad (30). As discussed above, the percussion plunger (20) is generally concentric, or cylindrical, and has a central bore (25) through which the percussion stem or tube (10) is slidably received. The percussion plunger (20) is also weighted to facilitate lowering of the probe (40), in this example a split-spoon sampler, to the bottom of the water body (if used for sampling water body sediments) and to drive the probe (40) to a desired depth for core extraction. This embodiment of the device is also useful, however, for core sampling on land as well as in water environments. Similar to the percussion plunger (20), the percussion pad (30) can be cylindrical with a central bore (35) through which the percussion stem or tube (10) is received, and is weighted. The percussion stem or tube (10) is affixed to the percussion pad (30), for instance by welding the percussion stem or tube (10) within the bore (35) of the percussion pad (30), or using other means to provide a secure connection. As discussed above these components can be fabricated using any suitable shape as would be apparent to one skilled in the art, although cylindrical shapes are used herein for purposes of illustration.

The probe (40), i.e. split-spoon sampler (40b, 40c, 40d), can be connected to the device (1') in a variety of ways, although three mechanisms are described herein for exemplary purposes. In the first non-limiting example (FIG. 12A), the split spoon sampler (40b) has a compatible threaded connector (200) that can be threaded directly onto threads at the end of the percussion stem or tube (10). The split spoon is therefore assembled and connected directly to the device (1') using the female threaded coupling end thereof.

In the second exemplary, yet non-limiting embodiment shown in FIG. 12B, a split spoon sampler (40c) which does not have a compatible thread is provided, and therefore requires an adapter to connect to the percussive driving apparatus. In this embodiment a coupling device (210) is provided that allows the percussion tube or stem (10) to be connected to a non-compatible thread (220) of the split spoon sampler (40c). The top half of the coupling device (210) has an internal female thread which matches the thread at the percussion end of the percussion tube or stem (10), and which is threaded internally to attach thereto. The bottom half of the coupling device (210) has an external male thread which matches the specific thread of the split spoon sampler (40c) to attach to the top end thereof.

In the third exemplary, yet non-limiting embodiment shown in FIG. 12C, a split spoon sampler (40d) which does not have a compatible thread is provided, and therefore requires an adapter to connect to the percussive driving apparatus. In this embodiment a coupling device (230) is provided that allows the percussion tube or stem (10) to be connected to a non-compatible thread (220) of the split spoon sampler (40d). The top half of the coupling device (230) has an internal female thread (235) which matches the thread at the percussion end of the percussion tube or stem (10), and which is threaded internally to attach thereto. The middle portion of the coupling device (230) consists of an annular percussion force stabilization disk (240) radially extending from the longitudinal axis of the coupling device (230), and which limits torque forces on the coupling device. The bottom half of the coupling device (230) has an external male thread (236) which matches the specific thread of the split spoon sampler (40d) to attach to the top end thereof.

In a further optional embodiment, in the event that greater depths of sediment core sample are required, additional lengths of split spoon can be attached using a coupling.

In one non-limiting application wherein the device (1') is used to obtain core samples from a water body, the entire sampling device (1') is lowered to the bottom of the water body until the split spoon (40b, 40c, 40d) touches the bottom sediment (90). The percussion plunger (20) is then raised and lowered to impact the percussion pad (30) until the split spoon (40b, 40c, 40d) penetrates the sediment (90) to the desired depth, or the percussion pad (30) impacts the sediment (90), or the substrate is so resistant that no further penetration is possible. The winch (160) (if used) is then employed to raise the entire device (1') to the surface where the split spoon sampler (40b, 40c, 40d) is removed and the sediment sample is retrieved therefrom. As in the above-described embodiments, rapidly raising the percussion plunger (20) so that it impacts the exit element (100) provides additional upward shock energy to help extract the split spoon sampler (40b, 40c, 40d) from the substrate (90).

Shielded Piezometer:

The percussive driving apparatus described herein can also be used with a shielded piezometer tip as will be described in further detail below.

Shielded piezometer tips (230) (see FIG. 13) are used to protect the piezometer from becoming contaminated by overlying layers of soil sediment prior to interception of the desired layer. A shield or sheath (250) covers the tip (260) and is kept in place by both the friction of an internal rubber ring (270) and the upward forces on the shield (250) while the tip (260) is being driven into the substrate. When the tip reaches the desired depth plus the length of the shield, the driving mechanism is retracted which pulls the tip out of the protective sheath (250) and exposes the piezometer to the strata containing the groundwater. On land and in shallow water situations the tip (230) is driven into the soil sediment using various mechanisms, such as hydraulic rams. In deep water or fast current situations it can be difficult and expensive using these conventional sampler driver techniques. The percussive driving apparatus described herein provides a useful alternative.

According to this embodiment of the invention, the probe (40) of the percussive driving apparatus is a shielded piezometer tip which is connected to the percussion stem or tube (10) in place of the piezometer described above and shown in FIGS. 1 to 10. Groundwater sampling is therefore undertaken by driving the probe (40), or in this case the shielded piezometer tip, into the terrain using percussive force and avoids the need for more cumbersome and expensive hydraulic mechanisms.

Figure 14:
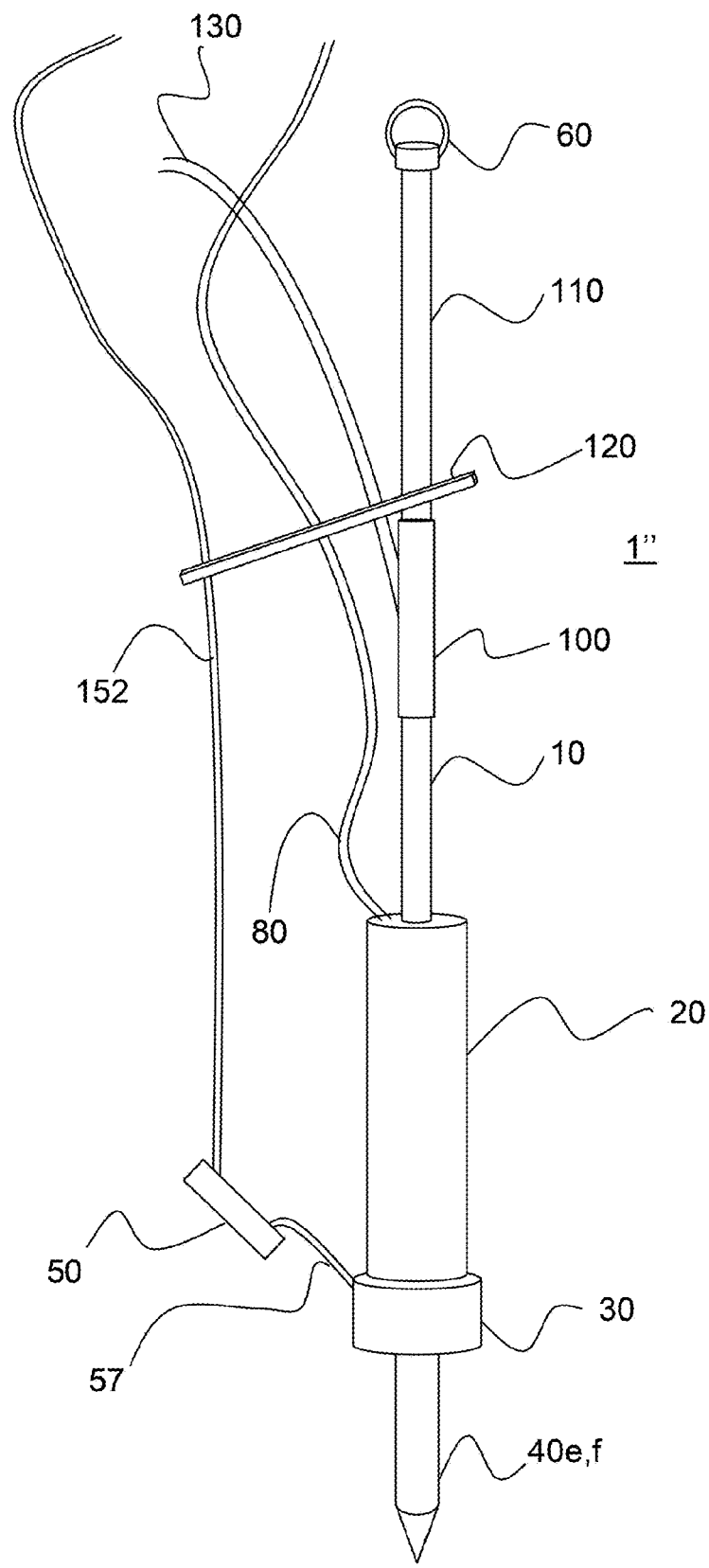
FIG. 14 shows a side perspective view of an example of the percussive driving apparatus used in conjunction with a groundwater sampling device having a shielded piezometer tip, in accordance with another embodiment of the present invention.

With the exception of the probe (40), the elements of the percussive driving apparatus are similar to those described above. Referring to FIG. 14, the device (1") includes similar elements to those shown in FIG. 1, including a percussion stem or tube (10), a percussion plunger (20) and a percussion pad (30). As discussed above, the percussion plunger (20) is generally concentric, or cylindrical, and has a central bore (25) through which the percussion stem or tube (10) is slidably received. The percussion plunger (20) is also weighted to facilitate lowering of the probe (40), in this example a shielded piezometer tip (40e, 40f), to the bottom of the water body (if used for sampling upwelling groundwater samples) and to drive the probe (40) to a desired depth for sampling. The addition of ballasts (70) above and below the percussion plunger may be included to increase mass and/or percussive force. This embodiment of the device is also useful, however, for groundwater sampling on land as well as in water environments. Similar to the percussion plunger (20), the percussion pad (30) can be cylindrical with a central bore (35) through which the percussion stem or tube (10) is received, and is weighted. The percussion stem or tube (10) is affixed to the percussion pad (30), for instance by welding the percussion stem or tube (10) within the bore (35) of the percussion pad (30), or using other means to provide a secure connection. As discussed above these components can be fabricated using any suitable shape as would be apparent to one skilled in the art, although cylindrical shapes are used herein for purposes of illustration.

The probe (40), i.e. shielded piezometer tip (40e, 40f), can be connected to the device (1") in a variety of ways, although two mechanisms are described herein for exemplary purposes. In the first non-limiting example (FIG. 15A), the shielded piezometer tip (40e) has a compatible threaded connector (290) that can be threaded directly onto threads at the end of the percussion stem or tube (10). The shielded piezometer tip (40e) is therefore assembled and connected directly to the device (1") using the female threaded coupling end thereof and is snugged up against the pad. The maximum depth of penetration is therefore the length of the shielded tip (40e), or, for greater depth of penetration an extension stem or tube (54) can be used (see FIG. 4).

Figure 15:
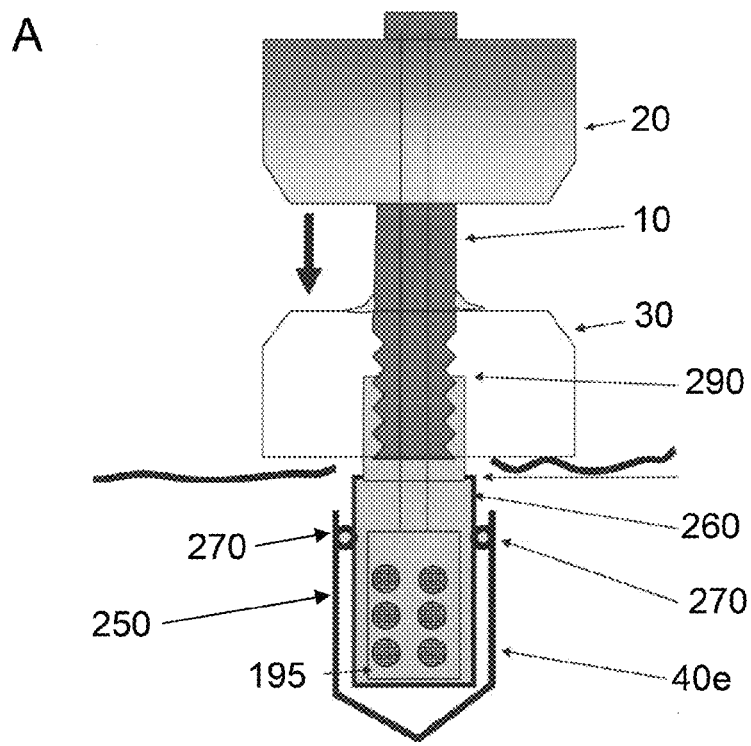
FIG. 15 shows a cross-sectional view of two examples (A and B) of embodiments of the groundwater sampling device shown in FIG. 14; following insertion into terrain or the bottom of a water body.
Figure 15:
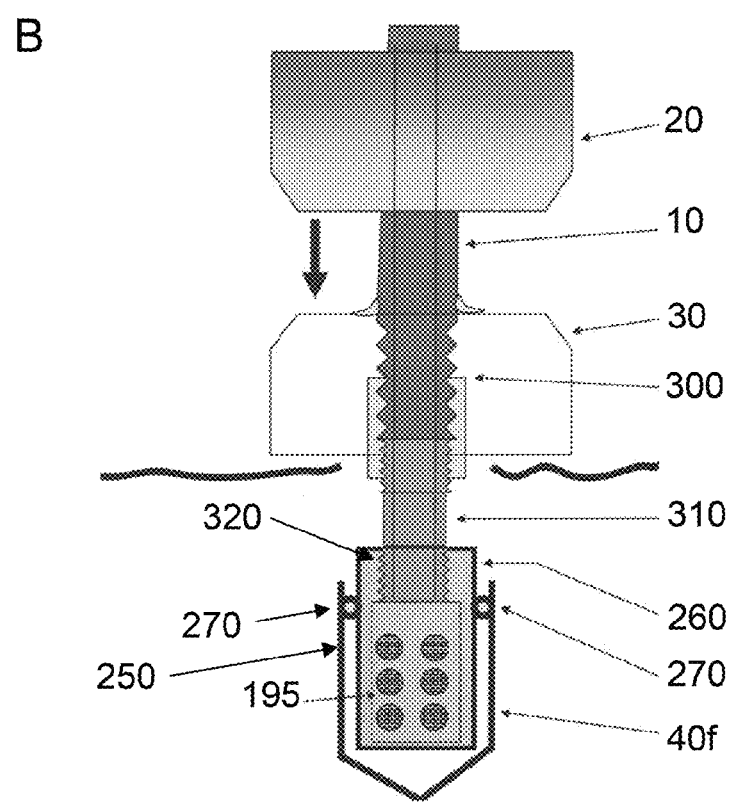

In the second exemplary, yet non-limiting embodiment shown in FIG. 15B, a shielded piezometer tip (40f) which does not have a compatible thread is provided, and therefore requires an adapter to connect to the percussive driving apparatus. In this embodiment the shielded piezometer tip (40f) can be connected to the percussion end of the percussive driving apparatus using a female to female coupling (300) and a male to male nipple (310). The appropriate sample tubing is first inserted into the percussion stem or tube (10) and exposed on the bottom end to a length longer than the female to female coupling (300) plus the male to male nipple (310). A female to female coupling (300) is attached to the bottom male end of the percussion stem or tube (10) and snug fit to it. A male to male nipple (310) of the desired length (for instance but not limited to about 12 cm or longer) is attached to the bottom end of the female to female coupling (300). The length of the male to male nipple (310) is dependant on the depth of penetration desired for the shielded piezometer tip (40f). The top threaded end of the shielded piezometer tip (40f) is attached via the internal nipple thereof to the exposed tubing.

The entire piezometer is then threaded via its internal threads (320) onto the bottom end of the male to male nipple (310). The external shield (250) is then slid over the piezometer tip (260) to protect it during insertion.

The piezometer shield (250) should have a sufficiently large internal rubber seal (270) to firmly grip the exterior of the piezometer in order to maintain a grip on the shield (250) while it is being lowered down the water column until it impacts with the bottom sediment.

In one non-limiting application wherein the device (1") is used to obtain groundwater samples from a water body, the entire sampling device (1") is lowered to the bottom of the water body until the piezometer shield (250) touches the bottom sediment (90), optionally using a winch (160). The percussion plunger (20) is then raised and lowered to impact the percussion pad (30) until the shielded piezometer tip (40e, 40f) penetrates the sediment (90) to the desired depth or until the percussion pad (30) impacts the sediment (90). The winch (160) (if used) is then employed to raise the entire apparatus to expose the piezometer tip (260). The piezometer shield (250) is sacrificed when the piezometer tip (260) is retracted. Reverse pulling on the percussion plunger (20) so that it impacts the exit element (100) will assist in retraction of the piezometer tip (260). The groundwater sample can then be extracted, optionally using the variable rate peristaltic pump (136).

One or more currently preferred embodiments have been described by way of example. It will be apparent to persons skilled in the art that a number of variations and modifications can be made without departing from the scope of the invention as defined in the claims.

What is claimed is:

1. A percussive driving apparatus for an environmental sampling or test device, the driving apparatus comprising:
   a percussion stem defining a central longitudinal cavity;
   an exit element connected to the percussion stem which defines an exit port through which tubing used in the device can exit said stem;
   a percussion plunger having a longitudinal bore through which the percussion stem is received, the percussion plunger being slidable along a length of the percussion stem;
   a lift element to permit lifting of the percussion plunger along at least a portion of said length of the percussion stem;
   a percussion pad affixed to the percussion stem at or near a first end thereof and configured to receive percussive driving force from the percussion plunger; and
   an attachment element to connect the apparatus to means for raising and lowering the apparatus when in use;
   wherein the percussion stem is adapted at the first end to connect to a probe for environmental sampling or testing.

2. The percussive driving apparatus of claim 1, wherein the percussion stem is further adapted at the first end to allow fluid to be conveyed from the probe into the central longitudinal cavity of the percussion stem.

3. The percussive driving apparatus of claim 2, wherein the percussion stem comprises tubing within the cavity for fluid transfer from the probe into and through said percussion stem cavity.

4. The percussive driving apparatus of claim 1, wherein the exit element is connected to the percussion stem at or near a second end of said percussion stem.

5. The percussive driving apparatus of claim 1, wherein said percussion plunger is slidable along a length of the percussion stem between said exit element and said percussion pad.

6. The percussive driving apparatus of claim 1, wherein said probe is a piezometer.

7. The percussive driving apparatus of claim 1, wherein said probe is a shielded piezometer.

8. The percussive driving apparatus of claim 1, wherein said probe is a split spoon sampler.

9. The percussive driving apparatus of claim 1, wherein the lift element comprises a lift cord attached to the percussion plunger.

10. The percussive driving apparatus of claim 1, wherein the percussion pad defines a recessed hole or groove on the bottom surface thereof, the recessed hole or groove having dimensions that facilitate connection of a connector element of the probe to the first end of the percussion stem and which encompass a junction between the probe and the first end of the percussion stem.

11. The percussive driving apparatus of claim 1, wherein an upper surface of the percussion pad defines a beveled edge at the outer perimeter thereof, said upper surface contacting said percussion plunger.

12. The percussive driving apparatus of claim 1, wherein a lower surface of the percussion plunger defines a beveled edge at the outer perimeter thereof, said lower surface contacting said percussion pad.

13. The percussive driving apparatus of claim 1, wherein the percussion pad comprises a camera anchoring element to secure a camera control line.

14. The percussive driving apparatus of claim 1, further comprising one or more percussion ballast, each having a longitudinal bore through which the percussion stem is slidably received.

15. The percussive driving apparatus of claim 1, further comprising an extension tube directly or indirectly connected to the percussion stem at or near a second end thereof.

16. The percussive driving apparatus of claim 1, wherein the attachment element is an anchor cap comprising a steel loop.

17. The percussive driving apparatus of claim 9, further comprising a mounting plate attached directly or indirectly via an aperture to the percussion stem and defining at least one additional aperture through which the lift cord is passed.

18. The percussive driving apparatus of claim 17, wherein the mounting plate defines a further aperture through which sample tubing is passed.

19. The percussive driving apparatus of claim 17, wherein the mounting plate defines a further aperture with an exit slot, to accommodate an underwater camera cable.

20. The percussive driving apparatus of claim 19, wherein the mounting plate further comprises a quick release clip to releasably attach said underwater camera cable.

21. A groundwater sampling device comprising a piezometer tip and a percussive driving apparatus, the driving apparatus comprising:
   a percussion tube defining a longitudinal cavity;
   an exit element connected to the percussion tube which defines an exit port through which tubing used in the device exits said percussion tube;
   a percussion plunger having a longitudinal bore through which the percussion tube is received, the percussion plunger being slidable along a length of the percussion stem;

a lift element to permit lifting of the percussion plunger along at least a portion of said length of the percussion tube;

a percussion pad affixed to the percussion tube at or near a first end thereof and configured to receive percussive driving force from the percussion plunger; and an attachment element to connect the apparatus to means for raising and lowering the apparatus when in use;

wherein the percussion tube is adapted at the first end to connect to the piezometer tip for groundwater sampling and to allow fluid to be conveyed from the piezometer tip into the percussion tube.

22. The groundwater sampling device of claim 21, wherein the tube comprises tubing therein for fluid transfer from the piezometer tip into and through said tube.

23. The groundwater sampling device of claim 21, wherein the exit element is connected to the percussion tube at or near a second end of said percussion tube.

24. The groundwater sampling device of claim 21, wherein said percussion plunger is slidable along a length of the tube between said exit element and said percussion pad.

25. The groundwater sampling device of claim 21, wherein said piezometer tip is a shielded or unshielded piezometer tip.

26. The groundwater sampling device of claim 21, wherein the lift element comprises a lift cord attached to the percussion plunger.

27. The groundwater sampling device of claim 21, wherein the percussion pad defines a recessed hole or groove on the bottom surface thereof, the recessed hole or groove having dimensions that facilitate connection of a connector element of the piezometer tip to the first end of the percussion tube and which encompass a junction between the piezometer tip and the first end of the percussion tube.

28. The groundwater sampling device of claim 21, wherein an upper surface of the percussion pad defines a beveled edge at the outer perimeter thereof, said upper surface contacting said percussion plunger.

29. The groundwater sampling device of claim 21, wherein a lower surface of the percussion plunger defines a beveled edge at the outer perimeter thereof, said lower surface contacting said percussion pad.

30. The groundwater sampling device of claim 21, further comprising an underwater camera and wherein the percussion pad comprises a camera anchoring element to secure a camera control line from said camera to said percussion pad.

31. The groundwater sampling device of claim 21, further comprising one or more percussion ballast, each having a longitudinal bore through which the percussion tube is slidably received.

32. The groundwater sampling device of claim 21, further comprising an extension tube directly or indirectly connected to the percussion tube at or near a second end thereof.

33. The groundwater sampling device of claim 21, wherein the attachment element is an anchor cap.

34. The groundwater sampling device of claim 26, further comprising a mounting plate attached directly or indirectly to the percussion stem and defining at least one aperture through which the lift cord is passed.

35. The groundwater sampling device of claim 34, wherein the mounting plate defines a further aperture through which sample tubing is passed.

36. The groundwater sampling device of claim 34, wherein the mounting plate defines a further aperture, optionally with an exit slot, to accommodate an underwater camera cable.

37. The groundwater sampling device of claim 36, wherein the mounting plate further comprises a quick release clip to releasably attach said underwater camera cable.

38. A core sampling device comprising a core sampling tip and a percussive driving apparatus, the driving apparatus comprising:

a percussion stem defining a central longitudinal cavity;

an exit element connected to the percussion stem which defines an exit port through which tubing used in the device can exit said stem;

a percussion plunger having a longitudinal bore through which the percussion stem is received, the percussion plunger being slidable along a length of the percussion stem;

a lift element to permit lifting of the percussion plunger along at least a portion of said length of the percussion stem;

a percussion pad affixed to the percussion stem at or near a first end thereof and configured to receive percussive driving force from the percussion plunger; and an attachment element to connect the apparatus to means for raising and lowering the apparatus when in use;

wherein the percussion stem is adapted at the first end to connect to the core sampling tip for environmental sampling.

39. The core sampling device of claim 38, wherein said core sampling tip is a split spoon sampler.

40. The core sampling device of claim 38, wherein the lift element comprises a lift cord attached to the percussion plunger.

41. The core sampling device of claim 38, wherein the percussion pad defines a recessed hole or groove on the bottom surface thereof, the recessed hole or groove having dimensions that facilitate connection of a connector element of the core sampling tip to the first end of the percussion stem and which encompass a junction between the core sampling tip and the first end of the percussion stem.

42. The core sampling device of claim 38, wherein an upper surface of the percussion pad defines a beveled edge at the outer perimeter thereof, said upper surface contacting said percussion plunger.

43. The core sampling device of claim 38, wherein a lower surface of the percussion plunger defines a beveled edge at the outer perimeter thereof, said lower surface contacting said percussion pad.

44. The core sampling device of claim 38, further comprising an underwater camera and wherein the percussion pad comprises a camera anchoring element to secure a camera control line from said camera to said percussion pad.

45. The core sampling device of claim 38, further comprising one or more percussion ballast, each having a longitudinal bore through which the percussion stem is slidably received.

46. The core sampling device of claim 38, further comprising an extension tube directly or indirectly connected to the percussion stem at or near a second end thereof.

47. The core sampling device of claim 38, wherein the attachment element is an anchor cap.

48. The core sampling device of claim 40, further comprising a mounting plate attached directly or indirectly to the percussion stem and defining at least one aperture through which the lift cord is passed.

49. The core sampling device of claim 48, wherein the mounting plate defines a further aperture with an exit slot, to accommodate an underwater camera cable.

50. The core sampling device of claim 49, wherein the mounting plate further comprises a quick release clip to releasably attach said underwater camera cable.

51. The core sampling device of claim 38, further comprising a coupling device to facilitate connection of said core sampling tip to the percussion stem.

52. The core sampling device of claim 51, wherein the coupling device further comprises an annular percussion force stabilization disk radially extending from the longitudinal axis of the coupling device, and which absorbs torque forces thereon.

\* \* \* \* \*